US009410853B2

(12) United States Patent
Zombo et al.

(10) Patent No.: US 9,410,853 B2
(45) Date of Patent: Aug. 9, 2016

(54) GUIDED WAVE THERMOGRAPHY METHODS AND SYSTEMS FOR INSPECTING A STRUCTURE

(71) Applicants: Paul J. Zombo, Cocoa, FL (US); James F. Landy, Cape Canaveral, FL (US); Joseph L. Rose, State College, PA (US); Steven E. Owens, Bellefonte, PA (US); Fei Yan, State College, PA (US); Cody J. Borigo, State College, PA (US)

(72) Inventors: Paul J. Zombo, Cocoa, FL (US); James F. Landy, Cape Canaveral, FL (US); Joseph L. Rose, State College, PA (US); Steven E. Owens, Bellefonte, PA (US); Fei Yan, State College, PA (US); Cody J. Borigo, State College, PA (US)

(73) Assignees: SIEMENS ENERGY, INC., Orlando, FL (US); FSB INC., State College, PA (US)

( * ) Notice: Subject to any disclaimer, the term of this patent is extended or adjusted under 35 U.S.C. 154(b) by 419 days.

(21) Appl. No.: 13/922,367

(22) Filed: Jun. 20, 2013

(65) Prior Publication Data
US 2013/0343424 A1    Dec. 26, 2013

Related U.S. Application Data

(60) Provisional application No. 61/662,487, filed on Jun. 21, 2012.

(51) Int. Cl.
*G01K 11/22* (2006.01)
*G01N 25/72* (2006.01)
*G01N 29/26* (2006.01)
*G01N 29/06* (2006.01)

(52) U.S. Cl.
CPC ............ *G01K 11/22* (2013.01); *G01N 25/72* (2013.01); *G01N 29/0672* (2013.01); *G01N 29/262* (2013.01); *G01N 2291/0425* (2013.01)

(58) Field of Classification Search
CPC . G01N 25/72; G01N 29/262; G01N 29/0672; G01N 2291/0425; G01K 11/22
USPC ................... 73/618, 598, 600, 602
See application file for complete search history.

(56) References Cited

U.S. PATENT DOCUMENTS

| | | | |
|---|---|---|---|
| 5,671,746 A * | 9/1997 | Dreschel ............... | B06B 1/0633 600/459 |
| 5,734,588 A | 3/1998 | Rose et al. | |
| 6,236,049 B1 * | 5/2001 | Thomas et al. ............ | 250/341.6 |
| 6,399,948 B1 | 6/2002 | Thomas et al. | |
| 6,684,681 B1 | 2/2004 | Zombo | |
| 6,836,670 B2 * | 12/2004 | Castrogiovanni et al. ..... | 455/558 |
| 6,998,616 B2 | 2/2006 | Favro et al. | |

(Continued)

OTHER PUBLICATIONS

Joseph L. Rose, "Ultrasonic Guided Waves in Structural Health Monitoring", Key Engineering Materials vols. 270-273 (2004) pp. 14-21, © 2004 Trans Tech Publications, Switzerland.

(Continued)

*Primary Examiner* — J M Saint Surin

(57) ABSTRACT

Methods and systems (10) based on guided wave thermography for non-destructively inspecting structural flaws that may be present in a structure (15). For example, such systems and methods may provide the ability to selectively deliver sonic or ultrasonic energy to provide focusing and/or beam steering throughout the structure from a fixed transducer location (12, 14, 16). Moreover, such systems and methods may provide the ability to selectively apply sonic or ultrasonic energy having excitation characteristics (FIGS. 11 and 12) which may be uniquely tailored to enhance the thermal response (FIGS. 5 and 7) of a particular flaw geometry and/or flaw location.

24 Claims, 6 Drawing Sheets

(56) References Cited

U.S. PATENT DOCUMENTS

| | | | |
|---|---|---|---|
| 7,057,176 B2 | 6/2006 | Rothenfusser et al. | |
| 7,064,331 B2 | 6/2006 | Rothenfusser et al. | |
| 7,122,801 B2 * | 10/2006 | Favro et al. | 250/341.6 |
| 7,131,331 B2 | 11/2006 | Bates | |
| 7,211,055 B2 * | 5/2007 | Diederich | A61N 7/02 601/2 |
| 7,516,663 B2 * | 4/2009 | Ringermacher et al. | 73/601 |
| 7,716,987 B2 * | 5/2010 | Sathish et al. | 73/589 |
| 7,751,989 B2 | 7/2010 | Owens et al. | |
| 7,938,008 B2 | 5/2011 | Owens et al. | |
| 7,974,791 B2 | 7/2011 | Broddegaard et al. | |
| 7,997,139 B2 | 8/2011 | Owens et al. | |
| 8,170,809 B2 | 5/2012 | Van Velsor et al. | |
| 8,201,454 B2 | 6/2012 | Paige | |
| 8,322,221 B1 * | 12/2012 | Sathish et al. | 73/606 |
| 2008/0245151 A1 * | 10/2008 | Roney | F01D 25/285 73/628 |
| 2009/0107758 A1 | 4/2009 | Moore | |
| 2010/0179425 A1 * | 7/2010 | Zadicario | A61B 8/0816 600/438 |
| 2010/0217544 A1 | 8/2010 | Yan et al. | |
| 2012/0119732 A1 | 5/2012 | Rose et al. | |
| 2012/0279308 A1 | 11/2012 | Yan et al. | |

OTHER PUBLICATIONS

Borigo et al., "Analysis of the Excitation Spectra of Annular and Comb Arrays for Ultrasonic Guided Wave Applications", ASNT Research Symposium, pp. 1-5, San Francisco, CA (2011).

Gavric, "Computation of Propagative Waves in Free Rail Using a Finite Element Technique", Journal of Sound and Vibration (1995) 185(3), pp. 531-543, France.

Quarry et al., Phase Velocity Spectrum Analysis for a Time Delay Comb Transducer for Guided Wave Mode Excitation, Review of Progress in Quantitative Nondestructive Evaluation vol. 20, pp. 861-868 (2001).

Solodov et al., "A local defect resonance to enhance acoustic wave-defect interaction in ultrasonic nondestructive evaluation", Applied Physics Letters, 99, pp. 211911-211911-3, (2011).

J.L. Rose, "Guided Wave Testing of Water Loaded Structures", Materials Evaluation vol. 61, No. 1, pp. 23-24, 2003.

Rose et al., "Ultrasonic vibration method for damage detection in composite aircraft components", IMAC XXX Conference, 9 pages, Jacksonville, FL (2012).

S.I. Rokhlin, "Resonance phenomena of Lamb waves scattering finite crack in a solid layer", J. Acoust. Soc. Am., 69 (4), pp. 922-928 (1981).

F. Yan, "Time delay comb transducers for aircraft inspection", The Aeronautical Journal, vol. 113, No. 1144, pp. 417-427 (2009).

Borigo et al., "Ultrasonic Guided Wave Vibration Formulation", Quantitative Nondestructive Evaluation Conference, 8 pages, Burlington, VT (2011).

R.B. Mignogna et al., "Thermographic investigation of high-power ultrasonic heating in materials", Ultrasonics, vol. 19, Issue 4, Jul. 1981, pp. 159-163.

Rheinfurth M et al: "Air-coupled guided waves combined with thermography for monitoring fatigue in biaxially loaded composite tubes" Composites Science and Technology Elsevier, IK, vol. 71, No. 5, Dec. 9, 2010, pp. 600-608, XP028176092, ISSN: 0266-3538, DOI:10 1016/J COMPSCITECH. 2010-12-012 [retrieved on Dec. 17, 2010] abstract paragraph [0004.] figures 1, 9.

* cited by examiner

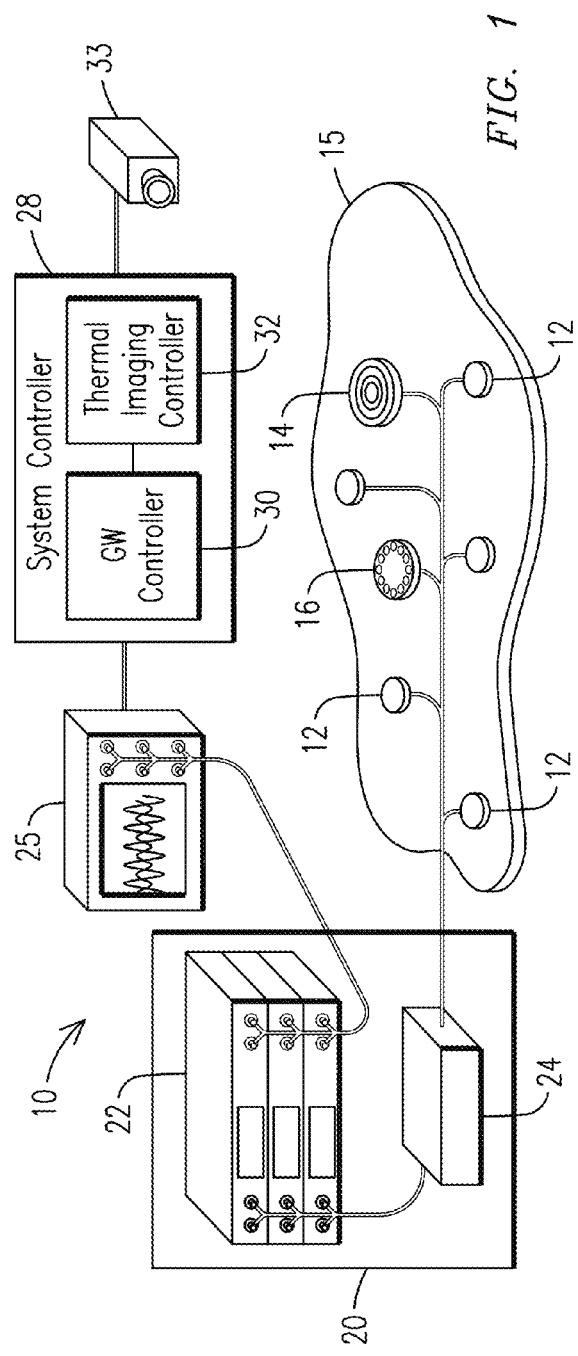
FIG. 1
FIG. 2
FIG. 3

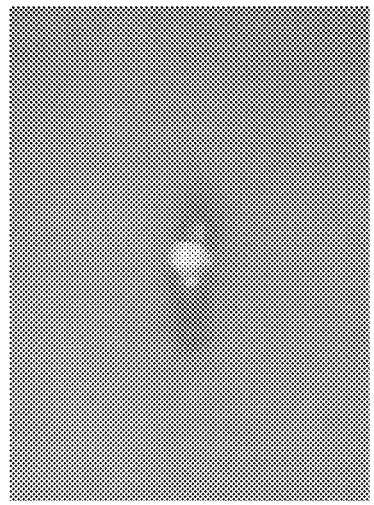
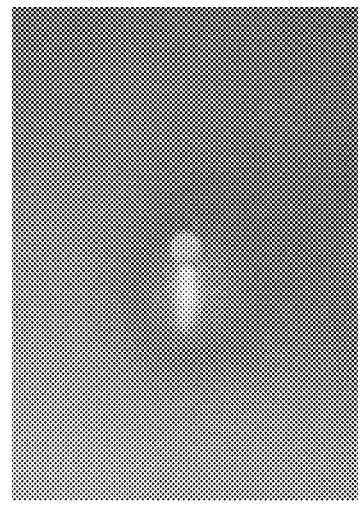
FIG. 7　　　　　　　　　FIG. 8
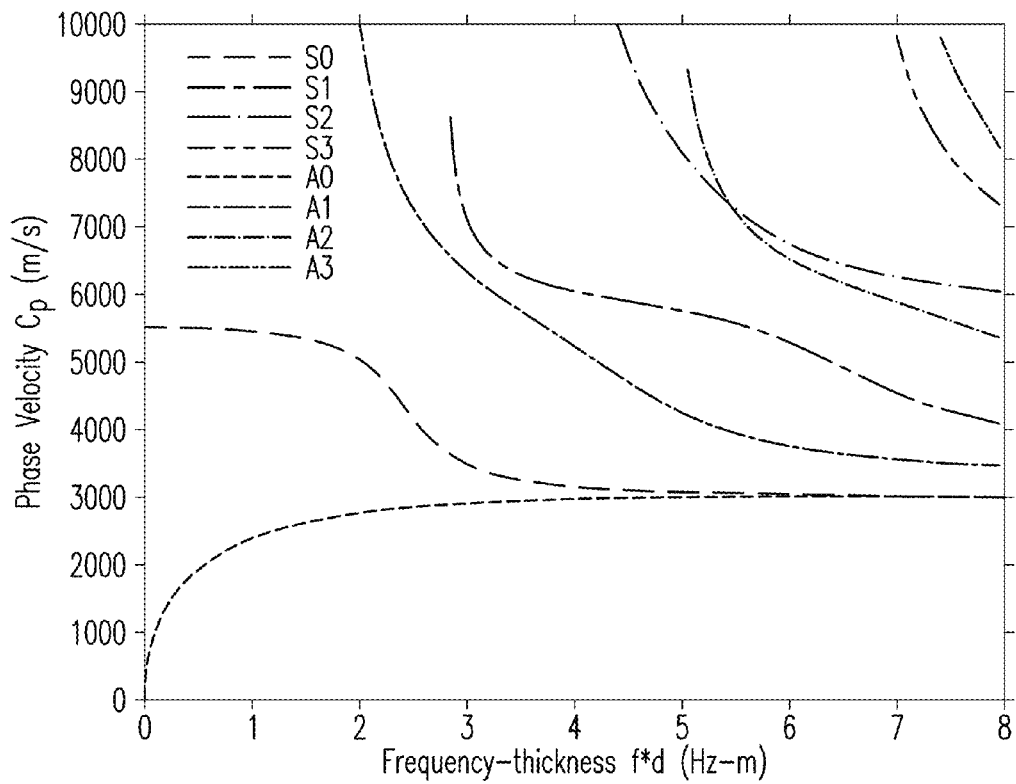
FIG. 9

GUIDED WAVE THERMOGRAPHY METHODS AND SYSTEMS FOR INSPECTING A STRUCTURE

This application claims benefit of the 21 Jun. 2012 filing date of U.S. provisional patent application 61/662,487, which is incorporated by reference herein.

FIELD OF THE INVENTION

The present invention is generally related to non-destructive inspection of structures, and, more particularly, to guided wave thermography methods and systems for inspecting structural flaws, which may be located in a structure.

BACKGROUND OF THE INVENTION

Thermographic imaging has proven to be a generally useful technique for detecting structural abnormalities. For example, when exciting a structure with flaws using relatively high ultrasonic power, frictional heating may be generated at the flaws. The flaws can then become detectable under a thermal infrared camera. However, structurally weak regions that may be part of the structure may be vulnerable when subjected to such high ultrasonic power, which could lead to break up of the structure being inspected. Thus, there is a need for further improvements in connection with systems and methods for inspecting a structure.

BRIEF DESCRIPTION OF THE DRAWINGS

The invention is explained in the following description in view of the drawings that show:

FIG. 1 is a schematic representation of a non-limiting embodiment of a guided wave thermography system, which may be used to practice aspects of the present invention.

FIG. 2 is an isometric view of one non-limiting embodiment of a multi-element transmitting-transducer, which may be used for transmitting ultrasonic guided waves through a structure being inspected in accordance with aspects of the present invention.

FIG. 3 is an isometric view of another non-limiting embodiment of a multi-element transmitting-transducer.

FIGS. 7 and 8 show comparative examples of thermal responses in a structure having two structural flaws disposed proximate an opening in the structure, where the response illustrated in FIG. 7, was driven with an appropriate excitation frequency and shows both structural flaws, while the response illustrated in FIG. 8 misses one of such structural flaws.

FIGS. 9 and 10 show non-limiting examples of dispersion curves illustrating a respective relationship between phase velocity (FIG. 9) and group velocity (FIG. 10) and guided wave mode and frequency for a given structure.

DETAILED DESCRIPTION OF THE INVENTION

Figure 4:
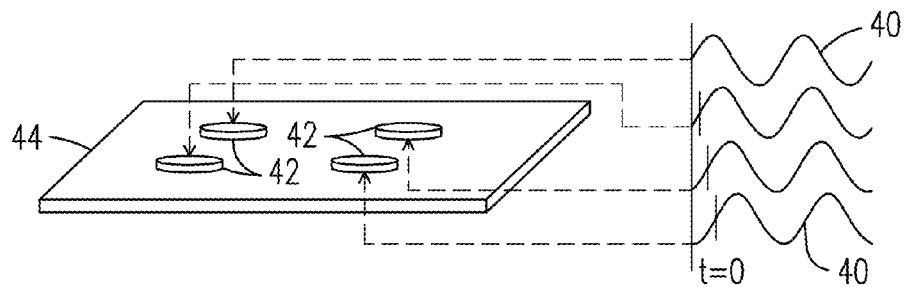
FIG. 4 is a schematic representation of a non-limiting embodiment for implementing phasing delays to excitation signals applied to transmitting-transducers to generate the ultrasonic guided waves.

The present inventors have innovatively recognized that existing acoustic/ultrasonic thermography systems are generally limited by the efficiency and effectiveness by which such systems are capable of inducing thermal responses indicative of structural flaws. The present inventors have further recognized a need of systems and methods that may be selectively optimized to efficiently cause thermal responses at structural flaws with relatively low excitation power. For example, systems and methods, which may be effective for high flaw detection sensitivity while selectively controlling the excitation energy to protect vulnerable regions which may be present in a structure being inspected.

In accordance with one or more embodiments of the present invention, methods and systems based on guided wave thermography for non-destructively inspecting structural flaws that may be present in a structure are described herein. For example, such systems may include the ability to selectively deliver sonic or ultrasonic energy to provide focusing and/or beam steering throughout the structure from a fixed transducer location. Moreover, such systems may include the ability to selectively apply acoustic or ultrasonic energy having excitation characteristics which may be uniquely tailored to enhance the thermal response of a particular flaw geometry and/or flaw location. In the following detailed description, various specific details are set forth in order to provide a thorough understanding of such embodiments. However, those skilled in the art will understand that embodiments of the present invention may be practiced without these specific details, that the present invention is not limited to the depicted embodiments, and that the present invention may be practiced in a variety of alternative embodiments. In other instances, methods, procedures, and components, which would be well-understood by one skilled in the art have not been described in detail to avoid unnecessary and burdensome explanation.

Furthermore, various operations may be described as multiple discrete steps performed in a manner that is helpful for understanding embodiments of the present invention. However, the order of description should not be construed as to imply that these operations need be performed in the order they are presented, nor that they are even order dependent unless otherwise do described. Moreover, repeated usage of the phrase "in one embodiment" does not necessarily refer to the same embodiment, although it may. Lastly, the terms "comprising", "including", "having", and the like, as used in the present application, are intended to be synonymous unless otherwise indicated.

The present inventors propose innovative utilization of sonic or ultrasonic guided waves for performing thermography inspection on a variety of structures, which in one non-limiting application may comprise components of a combustion turbine engine, such as blades, vanes, etc. Ultrasonic guided waves comprise multi-mode structural resonances that propagate in a bounded structure, which effectively functions as a waveguide. The versatility provided by ultrasonic guided waves is practically unlimited compared to traditional bulk waves, and, consequently, analogies to inspection techniques based on propagation of bulk waves would be inappropriate. For example, in accordance with non-limiting aspects of the present invention, the present inventors have recognized that ultrasonic guided waves may be selectively controlled to provide beam steering, focusing, and/or guided wave mode selection for delivery of sonic or ultrasonic energy to any desired region throughout the structure, something not feasible with bulk waves from a single transmitting-transducer location. The present inventors have additionally recognized that guided waves are not restricted to the so-called point of coupling-in for the ultrasound exciter, as mentioned in U.S. Pat. No. 7,974,791 col. 3, line 11, which can lead to burdensome and costly inspection procedures involving multiple relocations of the exciter throughout the structure being inspected.

Aspects of the present invention utilize guided waves to selectively deliver acoustic sonic or ultrasonic energy throughout the structure, which can cause a thermal response (e.g., heating) upon impingement with a structural flaw which may be located in the structure. As elaborated in greater detail below, the thermal response induced by the sonic or ultrasonic energy can be detected with a thermal imaging system.

FIG. 1 is a schematic representation of a guided wave thermography system 10, which may be used to practice aspects of the present invention. In one non-limiting embodiment, system 10 may include one or more transmitting-transducers coupled to a structure 15 (an object being inspected) for transmitting ultrasonic guided waves through the structure. The transmitting-transducers may be arranged as a distributed array of single-element transmitting-transducers 12; or may comprise multi-element transmitting-transducers, such as an annular array transducer 14 comprising a plurality of individually-actuated transmitting elements 17 (as may be better appreciated in FIG. 2); or a circular array transducer 16 comprising a plurality of individually-actuated transmitting elements 19 (as may be better appreciated in FIG. 3). The transmitting-transducers could include, but are not limited to piezo-stack transducers, piezo-ceramic bars or disks, magnetostrictive transducers, electromagnetic acoustic transducers (EMATs), controlled mechanical impact devices, piezo-composites, etc. It will be appreciated that aspects of the present invention are not limited to any particular configuration for the transmitting-transducers, or to any particular shape of structure 15. Accordingly, the configuration of transmitting-transducers, or the shape of structure 15 as illustrated in the figures should be construed in an example sense and not in a limiting sense.

System 10 may further include a signal conditioner 20, which in one non-limiting embodiment may be configured to provide appropriate signal amplification by way of one or more amplifier circuits 22, and impedance matching by way of one or more impedance matching networks 24 to electrical signals which may be respectively applied to transmitting-transducers 12, 14, 16 from a signal generator 25 (e.g., a multi-channel signal generator). A system controller 28 may include a guided wave controller 30, (labeled GW controller) which may be configured to control signal generator 18, such as may be configured to control one or more signal parameters of one or more signals that may be applied to the one or more transmitting-transducers to generate the ultrasonic guided waves transmitted through structure 15. Non-limiting examples of signal parameters that may be controlled to determine signal characteristics for the signals that may be applied to the one or more transmitting-transducers may comprise a phase delay, a frequency, and a combination of phase delays and frequencies, such as may involve a phase delay sweep, frequency sweep or both. System controller 28 may further include a thermal imaging system comprising a thermal imaging controller 32 to control a thermal imaging sensor 33 (e.g., an infrared (IR) camera) configured to sense a thermal response indicative of the flaw.

It will be appreciated that for thermography to effectively detect structural flaws, the magnitude of certain vibration variables (e.g., in-plane displacement, shear stress, etc.) appropriate to the geometry and/or the spatial orientation of a given structural flaw, should be set sufficiently high in the immediate vicinity of the given flaw to ensure that a sufficient thermal response (e.g., heating) is induced.

As will be appreciated by one skilled in the art, during ultrasonic vibration of plate-like or other waveguide-like structures, the magnitude of the generated vibration fields can vary throughout such structures. For example, such variations may occur both through the thickness of the structure and as a function of distribution relative to the other dimensions of the structure. Accordingly, the variation in the vibration fields can lead to regions of relatively high stress, displacement, etc., as well as to regions of practically no stress, displacement, etc. In order for a structural flaw located in a given region of the structure to be appropriately thermally excited, the pertinent vibration variables of the vibration field delivered to such a region should have sufficiently high amplitude. As suggested above, the pertinent vibration variables may vary depending on the geometry of the structural flaw and/or the spatial orientation of the flaw.

In one non-limiting embodiment, control of phase delay and/or frequency (e.g., phase delay and/or frequency sweep) may be performed on the signals (e.g., continuous signals) applied to the one or more transmitting-transducers coupled to structure 15. This phasing action when performed on the transmitting-transducers may be conducive to enhanced spatial selectivity for the locations of low or high sonic or ultrasonic energy throughout such structures (e.g., enhanced spatial selectivity for the location of nodes for enhancing the intensity of the sonic or ultrasonic energy delivered to a given region of the structure, and the location of anti-nodes for attenuating the intensity of the sonic or ultrasonic energy delivered to other regions of the structure). In one non-limiting embodiment, the phasing can be performed in conjunction with frequency sweeping to provide maximum spatial selectivity to intensity variation throughout the structure of the generated vibration fields. The combination of signal phasing and frequency sweeping effectively allows spanning of a multi-dimensional phasing-frequency space. This allows for an ability to form a relatively greater range of vibration states—which for example may be selectively formed throughout the structure being inspected—than would be feasible if operating at a single frequency, or just performing frequency sweeping. These vibration states allow substantial versatility regarding selectivity of different vibration fields throughout the thickness of the structure, such as displacement wavestructure, stress wavestructure, vibration mode shape, etc. This is conducive to an increased likelihood of detecting a broad range of structural flaws, regardless of structural flaw geometry, depth, and other flaw characteristics.

FIG. 4 is a schematic representation of one non-limiting embodiment for implementing a respective phase delay on signals 40 respectively applied to single-element transmitting-transducers 42 distributed on a structure 44 being inspected. In this embodiment, continuous wave signals 40 may be respectively applied to transmitting-transducers 40 each having a different phase delay. Without limiting aspects of the present invention to any particular theory of operation, it is believed that in this case the effect of phasing may be to excite various natural modes of the structure by changing a loading distribution across its surface. For readers desirous of general background information in connection with this phasing approach reference is made to U.S. Pat. No. 8,217,554, which discloses an example application of phasing for achieving effective structural coverage for purposes of ultrasonic deicing, which patent is incorporated by reference herein.

Figure 5:
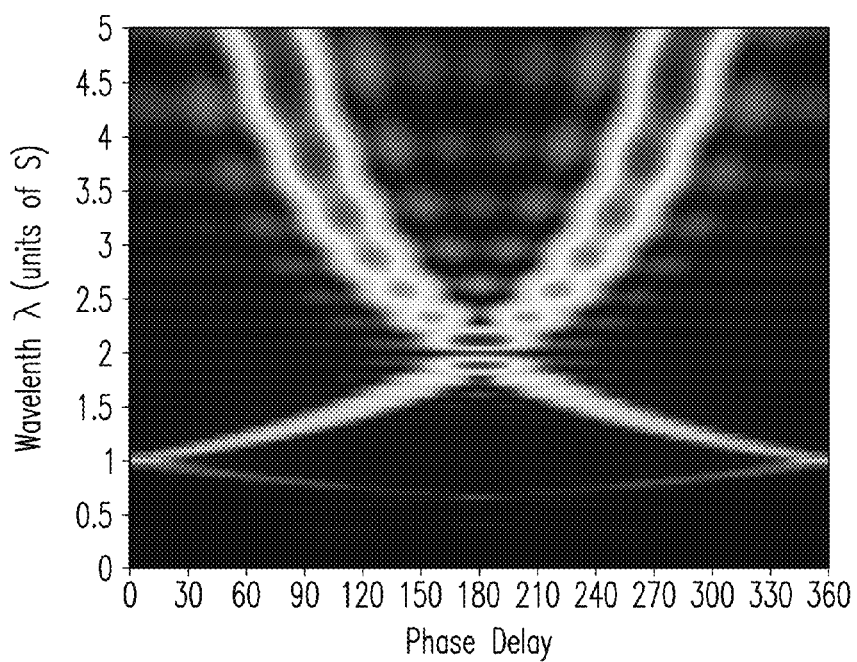
FIG. 5 is a plot of a non-limiting example of a spectral response in a wavelength domain as a function of phase delay, which may result from guided waves generated by a multi-element transmitting-transducer.
Figure 6:
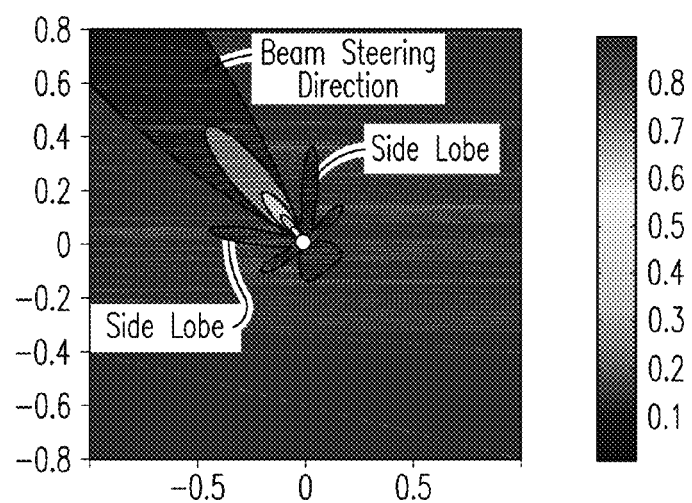
FIG. 6 is a plot of a non-limiting example of a steerable guided wave, which may result from guided waves generated by a multi-element transmitting-transducer.

Phasing can also be accomplished by utilizing one or more multi-element actuators, examples of which would include annular array transducers or other multi-element actuators as shown in FIGS. 2 and 3. Once again without limiting aspects of the present invention to any particular theory of operation, it is believed that in this case the effect of phasing may be an ability to selectively excite different guided wave modes based on the phasing characteristics and/or the geometry of the closely-spaced actuator elements. For example, the generated guided waves will lead to the excitation of ultrasonic vibration modes associated with such guided waves. The combination of signal phasing and frequency is believed to effectively allow covering a substantial portion of a dispersion curve. See for example FIG. 5, showing a non-limiting example of a spectral response in a wavelength domain as a function of phase delay, which may result from guided waves generated by a multi-element annular array transducer. This may provide significant selectivity in both the through-thickness and distributed excitation fields throughout the structure In another non-limiting embodiment, in lieu of continuous signals, respective streams of pulses may be applied to the one or more single or multi-element transmitting-transducers coupled to the structure being inspected. In this embodiment, transient guided waves may be propagated throughout the structure to avoid causing steady-state vibration. This may be accomplished by applying relatively narrow, high-power excitation pulses. It is contemplated that a similar effect (e.g., no steady-state vibration) may be achieved in applications involving large and/or attenuative structures, in which there may be insufficient interaction with the boundaries of the structure to induce structural resonance. These excitation pulses may be repeated at a repetition frequency sufficient to cause the accumulation of thermal energy in the vicinity of a given structural flaw to allow the thermal imaging system to detect the structural flaw. As will be appreciated by one skilled in the art, appropriate imaging techniques may be utilized to increase the signal-to-noise ratio and detect relatively weak thermal gradients.

Transient guided wave thermography is believed to provide a number of benefits over traditional steady-state thermography, including without limitation beam steering, focusing, and guided wave mode selection. In one non-limiting embodiment, guided wave beam steering in plates and other waveguide-like structures could be utilized by applying appropriate phase delays to an array of transmitting-transducers. Thus, the respective locations of excited regions of the structure may be selectively controlled. Guided wave focusing may also be accomplished by applying appropriate phase delays to the transmitting-transducers, such as to achieve constructive interference at a desired location of the structure. It is contemplated that the transient guided wave modes that can be generated throughout the structure may be selected by appropriate transducer design and/or phased array operation, such as to achieve optimal excitation of certain types of structural flaws. This mode selection may also be used to avoid damage to the structure being inspected by selecting guided wave modes with reduced acoustic or ultrasonic energy, stress, displacement, etc. at vulnerable regions throughout the structure.

By generating appropriate guided wave modes at the appropriate frequencies, the transient guided waves may be selected to have properties, such as displacement wavestructure, stress wavestructure, etc., which may be advantageously chosen to increase the likelihood of exciting particular structural flaws in the structure and in turn detect a thermal response via the thermal imaging system. The selection of specific guided wave modes can also be performed to selectively moderate the intensity of sonic or ultrasonic energy applied to a given region of the structure to cause enough local heating at the structural flaw to allow thermal imaging while avoiding damage growth due to excess mechanical excitation of the flaw. Additionally, phasing can be applied to multiple transmitting-transducers or transmitting elements to achieve selective beam steering and/or focusing throughout the structure, such as to regions in which constructive wave interference may be utilized to increase the amplitude of the guided wave field delivered to such regions. In one non-limiting embodiment, aspects of the present invention, such as formation of appropriately configured excitation fields selectively applied to one or more regions the structure, may be effective for gaining enhanced quantitative information in connection with structural flaws that may be present at such regions, such as may allow characterizing dimensions of the flaws, e.g., characterizing depth, length and width of a given flaw.

The description below will proceed to discuss aspects where guided wave thermography may exploit certain characteristics of the resonances of the structural flaws. Certain structural flaws, e.g., delaminations, cracks, etc., may have relatively high-frequency resonances associated with them that are independent of the lower-frequency resonances of the structure in which they are embedded. It has been shown that the local thermal response (e.g., at the structural flaw) at the flaw resonances can be substantially greater than the local response at the resonant frequencies of the entire structure. In one non-limiting embodiment, these characteristics of such flaw resonances can be exploited by exciting the structure at these relatively higher frequencies to maximize the local heating of the structural flaw for visualization via thermal imaging.

Significant improvements in response can be obtained by focusing guided wave energy via phased arrays with the appropriate frequency and wavestructure onto the flaw. It should be noted that the appropriate frequency of excitation can excite certain structural flaws and not others, as depicted in FIGS. 7 and 8. Therefore, the appropriate frequencies of excitation in conjunction with appropriate guided wave focusing can be used to thermally excite any flaws in the structure.

If the expected location of the flaw is known a priori, guided waves could be focused on that location at various frequencies using appropriate time delays. If the location of the flaw is unknown, the same phased arrays could be utilized to selectively move the focal spot on the structure while sweeping frequency. The frequency range of guided wave excitation which may be utilized in an thermography inspection embodying aspects of the present invention may be determined by the expected dimensions of suspected flaw(s) in a given structure. For most flaws, such frequencies may be located near or in the ultrasonic range and would be greater than the lower-order resonances of the structure in which they occur.

In one non-limiting embodiment, a structure being inspected may be a multi-part structure subject to different vibrational tolerances. The guided sonic or ultrasonic waves may be controlled so that sonic or ultrasonic energy delivered throughout such a multi-part structure appropriately meets the different vibrational tolerances of the multi-part structure. For example, this would allow inspecting a region in the structure having a relatively high vibrational tolerance while meeting the tolerances of other regions, which may be subject to a lower vibrational tolerance. Similarly, this would allow appropriately controlling the sonic or ultrasonic energy, which may be necessary for inspecting the regions subject to the lower vibrational tolerances.

In one non-limiting embodiment, it is contemplated that one may interspersedly or simultaneously apply different guided wave modes or wavestructures to a given region of a structure. For example, in the case of a relatively wide flaw, one may apply a first guided wave excitation with the wavestructures configured to induce compression at the edges of the flaw, and additionally one may also apply a second guided wave excitation with the wavestructures configured to induce shear between the compressed edges of the flaw. The two guided wave excitations can be applied interspersedly or simultaneously. This application of different guided wave excitations would allow detection of flaw geometries that otherwise could be missed due to a weak thermal response.

In one non-limiting embodiment, it is contemplated that the sensing of the thermal response by the thermal imager may be synchronized (e.g., lock-in, as may involve frequency lock, phase lock) relative to a frequency or phasing of the stream of excitation pulses which may be applied to the one or more transmitting transducers. It is further contemplated that such a frequency may comprise a time-varying frequency (e.g., a chirping frequency). This temporal synchronicity is believed to enhance a signal-to-noise ratio in connection with the sensing of the thermal response by the thermal imager. In one example embodiment, the synchronicity may be performed relative to an expected energization time of a region being excited in response to the guided sonic or ultrasonic waves.

Figure 17:
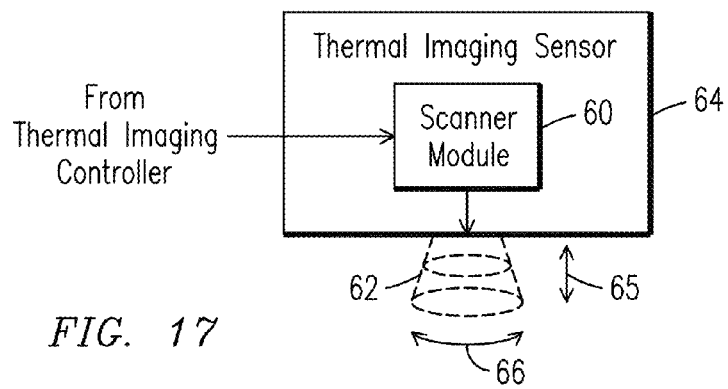
FIG. 17 is a non-limiting embodiment of a thermal imaging sensor including a scanner module that may allow dynamically tracking in real time an energization profile that may be formed throughout a structure being inspected in response to guided waves applied to the structure.

In one non-limiting embodiment, it is contemplated to control the sensing of the thermal response by the thermal imaging sensor based on an expected energization profile throughout the structure in response to an applied guided wave excitation or wavestructure. For example, a model of a structure to be inspected may be used to determine a priori how certain guided waves (e.g., based on wavestructure, guided wave mode, structure boundaries, etc.) are expected to deliver sonic or ultrasonic energy throughout the given structure. This may be used to determine a priori expected focal locations of sonic or ultrasonic energy which may be formed throughout the given structure. As illustrated in FIG. 17, a scanner module 60 (as may comprises software, hardware or combination of software and hardware) may be responsive to one or more control signals from thermal imaging controller 32 (FIG. 1) so that scan optics 62 (e.g., lens system, etc.) of a thermal imaging sensor 64 may be actuated to provide optical focusing and/or steering, as conceptually represented by lines 65 and 66, onto the expected focal locations, (e.g., form a field of view directed onto the expected focal locations).

In another example embodiment, in the event such focal locations are moved in real-time during an inspection (e.g., in response to transducer phasing and/or frequency sweeping), then scanner module 60 may be configured to be responsive to control signals from thermal imaging controller 32 (FIG. 1) so that sensing optics 62 may be actuated to dynamically track the movement of such focal locations. In either case, this controlled scanning would allow the thermal imaging sensor to achieve an improved signal-to-noise ratio in connection with the acquisition of the thermal response. For example—in lieu of having to monitor the entire structure being inspected—this allows to perform a smart scanning of the structure being inspected in response to a modeled (or real-time) energization profile formed in response to the specific guided waves applied to the structure. In one non-limiting example, more than one thermal imaging sensor may be controlled by the thermal imaging controller to dynamically track in coordinated fashion the movement of such focal locations.

Guided Waves Theoretical Underpinnings

Figure 10:
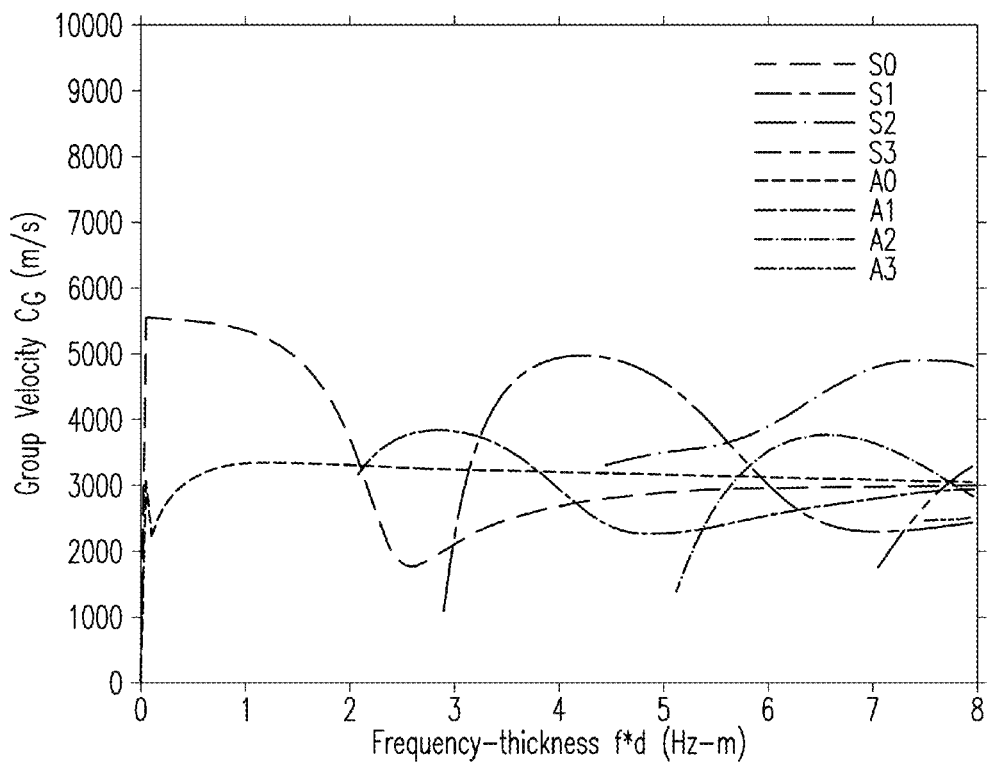
Figure 11:
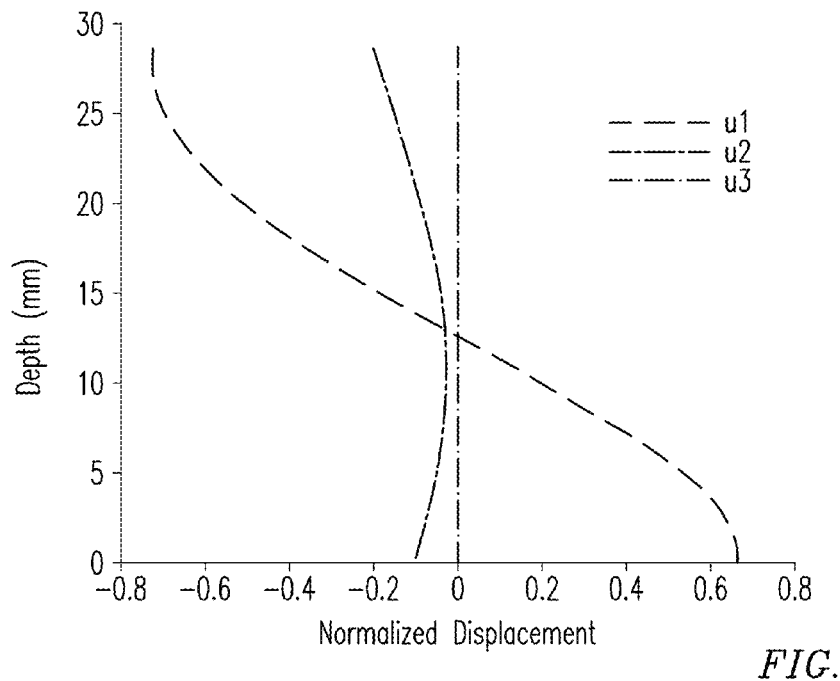
FIGS. 11 and 12 show non-limiting examples of guided waves comprising different wavestructures.
Figure 12:
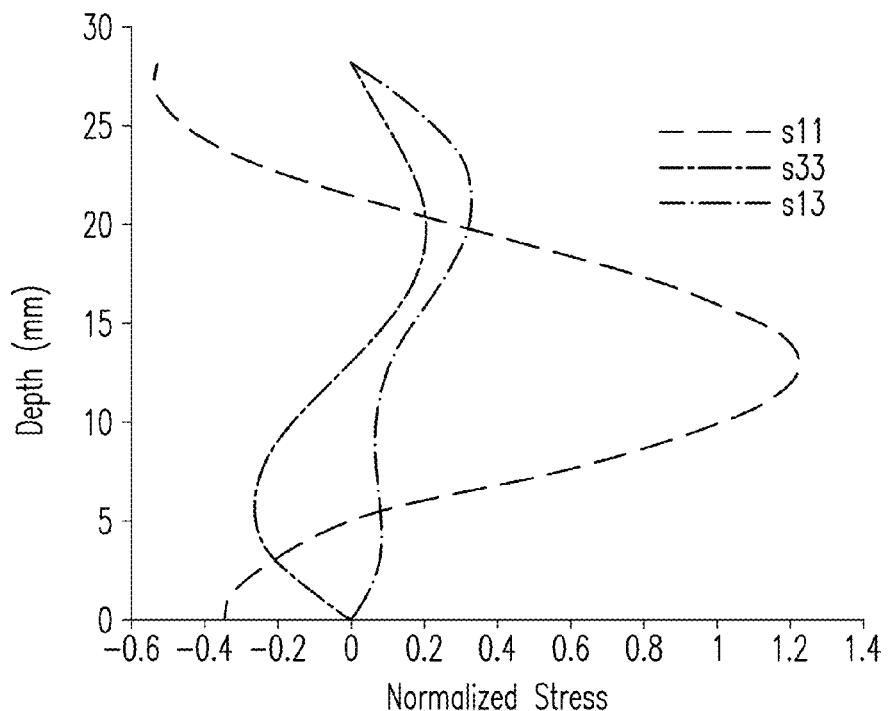

Guided waves may be defined as elastic waves propagating in a medium (a waveguide structure) in which distinct wave modes can exist that satisfy the boundary conditions of the waveguide structure. Guided waves differ from traditional bulk waves at least by the fundamental fact that an infinite number of distinct wave modes may exist with wavestructures (e.g., displacement, stress, energy, etc. distributions through the thickness of the waveguide) that may vary as a function of mode and/or frequency. Dispersion curves, such as those shown in FIGS. 9 and 10, illustrate a relationship between phase (or group) velocity and mode and frequency for a given structure. Each waveguide has its own unique set of dispersion curves, which may be useful for identifying various mode-frequency possibilities in a waveguide. Wavestructure variations can yield substantial flexibility for utilizing guided waves, since, for example, particular wave mode and/or frequency combinations can be selected with desirable properties through the thickness of the structure. Examples of guided waves comprising different wavestructures are shown in FIGS. 11 and 12. Energy distributions across the thickness of a waveguide, for example, could show where the sonic or ultrasonic energy may be focused; hence producing enhanced local heating of a structural flaw at a particular depth. This may provide a choice for generating transient guided waves, which after multiple reflections from the structural boundaries can lead to the formation of an ultrasonic vibration state. Although focal zones could change, theoretically-driven experimentation could be used to establish such zones. For readers desirous of gaining further details in connection with guided waves, reference is made to textbook by J. L. Rose, Titled *Ultrasonic Waves in Solid Media*, available from Cambridge University Press, New York, N.Y. (1999), which textbook is incorporated by reference herein.

Ultrasonic Vibration and the Relation to Transient Ultrasonic Guided Waves

Ultrasonic vibration may be characterized as the steady-state vibration of a structure at ultrasonic frequencies. In the context of disclosed embodiments, this vibration refers to vibration in waveguide-like structures, such as plates, pipes, shells, etc. While more common low-frequency vibration often presumes simplified field variation throughout the thickness of the structure, at ultrasonic frequencies such presumptions do not apply. In fact, there can be significant variations in displacement, stress, etc., throughout the thickness of a waveguide-like structure under ultrasonic vibration. It can be shown that such variations through the thickness for orthogonal natural modes of vibration of such structures are relatable to the wavestructures of guided waves in that structure at the resonant frequencies of the plate. For certain structures it can be shown that the orthogonal natural modes of vibration of the structure are comprised of a combination of guided wave modes propagating in the structure and creating a resonance. This relationship between ultrasonic vibration and guided waves can be exploited for purposes of thermography, as explained in greater detail below.

The simplest case of such ultrasonic guided wave vibration can be developed for a semi-infinite plate-like structure, although this can be expanded to higher-order structures, such as for the bar structure illustrated in connection with FIG. 14.

The elastic field that satisfies the harmonic equilibrium condition of a semi-infinite plate-like structure in steady-state vibration can be expanded as a superposition of propagating and evanescent guided wave modes traveling in the positive and negative x-directions. This can be written in terms of stresses σ as follows:

$$(x, z) = \sum_{\mu=1}^{\infty} \alpha_\mu \overline{\sigma}_\mu(z) e^{i(k_\mu x - \omega t)} + \sum_{\mu=1}^{\infty} \alpha'_\mu \overline{\sigma}_\mu(z) e^{i(k_\mu(x-L) - \omega t)}, \quad (1)$$

in which $\mu$ signifies the guided wave mode number, $\alpha$ and $\alpha'$ are the relative complex amplitude coefficient for each mode in the + and −x-directions, k is the wavenumber, L is the length of the plate, $\omega$ is the angular frequency, and $\overline{\sigma}$ is the transverse stress field (i.e. wavestructure) solution for each guided wave mode. The first term corresponds to waves traveling in the +x-direction and the second term to waves traveling in the −x-direction.

Figure 13:
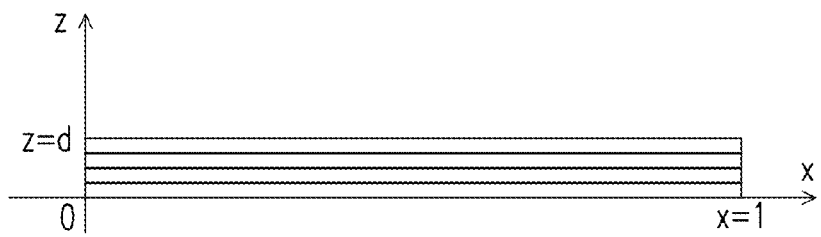
FIG. 13 shows a non-limiting example for conceptualizing a discretization of a semi-infinite plate structure in the thickness dimension, in which a number of discretization nodes were used.

The plate was then discretized with N nodes (e.g., five nodes) along the thickness direction, as shown in FIG. 13, and a semi-analytical finite element (SAFE) method was utilized to develop the dispersion curves and wavestructure solutions for the desired frequency range in the structure. The result of a SAFE dispersion analysis with N nodes is a set of 3N guided wave solutions in each x-direction.

All six possible combinations of the three classical boundary conditions (free, simply-supported, and clamped conditions) for the semi-infinite plate were successfully considered. The free-free boundary conditions, given as one non-limiting example, are as follows:

$$\begin{cases} \sigma_{xx}(x=0, z) = \sigma_{xx}(x=L, z) = 0 \\ \sigma_{xz}(x=0, z) = \sigma_{xz}(x=L, z) = 0 \\ \sigma_{xy}(x=0, z) = \sigma_{xy}(x=L, z) = 0. \end{cases} \quad (2)$$

Upon applying the boundary conditions of equation (2), by the collocation principle, to the discretized equation (1), a matrix equation is developed as a function of frequency:

$$\begin{bmatrix} \sigma_{xx}^1(z_1) & \cdots & \sigma_{xx}^{3N}(z_1) & \sigma_{xx}^1(z_1)e^{-ik_1 L} & \cdots & \sigma_{xx}^{3N}(z_1)e^{-ik_{3N} L} \\ \sigma_{xz}^1(z_1) & \cdots & \sigma_{xz}^{3N}(z_1) & \sigma_{xz}^1(z_1)e^{-ik_1 L} & \cdots & \sigma_{xz}^{3N}(z_1)e^{-ik_{3N} L} \\ \vdots & \vdots & \vdots & \vdots & \vdots & \vdots \\ \sigma_{xy}^1(z_N) & \cdots & \sigma_{xy}^{3N}(z_N) & \sigma_{xy}^1(z_N)e^{-ik_1 L} & \cdots & \sigma_{xy}^{3N}(z_N)e^{-ik_{3N} L} \\ \sigma_{xx}^1(z_1)e^{ik_1 L} & \cdots & \sigma_{xx}^{3N}(z_1)e^{ik_{3N} L} & \sigma_{xx}^1(z_1) & \cdots & \sigma_{xx}^{3N}(z_1) \\ \sigma_{xz}^1(z_1)e^{ik_1 L} & \cdots & \sigma_{xz}^{3N}(z_1)e^{ik_{3N} L} & \sigma_{xz}^1(z_1) & \cdots & \sigma_{xz}^{'3N}(z_1) \\ \vdots & \vdots & \vdots & \vdots & \vdots & \vdots \\ \sigma_{xy}^1(z_N)e^{ik_1 L} & \cdots & \sigma_{xy}^{3N}(z_N)e^{-ik_{3N} L} & \sigma_{xy}^1(z_N) & \cdots & \sigma_{xy}^{3N}(z_N) \end{bmatrix} \begin{Bmatrix} \alpha_1 \\ \alpha_2 \\ \alpha_3 \\ \vdots \\ \alpha_{6N} \end{Bmatrix} = \begin{Bmatrix} 0 \\ 0 \\ 0 \\ \vdots \\ 0 \end{Bmatrix} \quad (3)$$

In equation (3), the vector of complex amplitudes $\alpha$ is the only unknown and is a function of frequency. This can be written in a simpler manner by representing the large matrix as $\Lambda$:

$$[\Lambda]\{\alpha\} = \{0\} \quad (4)$$

Thus all nontrivial solutions to this matrix equation must correspond to the frequencies at which the determinant of $\Lambda$ is equal to zero:

$$|\Lambda| = 0 \quad (5)$$

This determinant was plotted as a function of $\omega$ and an iterative root-finding algorithm was used to locate the frequencies at which equation (5) is approximately satisfied. These frequencies are the natural resonant frequencies of the structure.

To determine the complex amplitude vector a associated with each natural resonant frequency, the nullspace of $\Lambda$ at each resonant frequency must be determined. However, since discrete values of $\omega$ and a finite number of guided wave modes were used in the superposition formulation, the matrix is not an exact representation of the system. Thus it is possible that all rows of the matrix can be linearly independent, which leads to a situation in which the rank of matrix $\Lambda$ is 6N and the nullspace of the matrix subsequently does not exist. To overcome this, an artificial eigenvalue problem can be developed as in equation (6).

$$\Lambda\alpha - \lambda\alpha = 0; \lambda = 0 \quad (6)$$

$$\lambda = \begin{Bmatrix} \lambda_1 \\ \lambda_2 \\ \vdots \\ \lambda_{6N} \end{Bmatrix}; \Phi = \begin{bmatrix} \alpha_1^{(1)} & \alpha_1^{(2)} & \cdots & \alpha_1^{(6N)} \\ \alpha_2^{(1)} & \alpha_2^{(2)} & \cdots & \alpha_2^{(6N)} \\ \vdots & \vdots & \cdots & \vdots \\ \alpha_{6N}^{(1)} & \alpha_{6N}^{(2)} & \cdots & \alpha_{6N}^{(6N)} \end{bmatrix} = [\alpha^{(1)} \alpha^{(2)} \cdots \alpha^{(6N)}] \quad (7)$$

This equation is identical to equation (4) as long as the eigenvalue $\lambda$ is equal to zero. To approximate this case, the eigenvalue equation (6) was solved and the smallest eigenvalue and corresponding eigenvector solution were considered. As long as this minimum eigenvalue is close to zero, the solution is a good approximation of equation (4) and thus (5) as well. Thus the complex amplitude vector for each resonant frequency is the eigenvector associated with the minimum eigenvalue, as shown in equations (8) and (9).

$$\lambda^{min} = \min(\lambda) \approx 0 \quad (8)$$

$$\alpha = \alpha^{(\lambda_{min})} = \begin{Bmatrix} \alpha_1 \\ \alpha_2 \\ \alpha_3 \\ \vdots \\ \alpha_{6N} \end{Bmatrix} \quad (9)$$

These solutions were then used to reconstruct the full stress or displacement vibration fields associated with each resonant frequency according to equations (10) and (11), respectively.

$$\sigma(x, z) = \sum_{\mu=1}^{3N} \alpha_\mu \overline{\sigma}_\mu(z) e^{i(k_\mu x - \omega t)} + \sum_{\mu=3N+1}^{6N} \alpha_\mu \overline{\sigma}_\mu(z) e^{i(k_\mu(x-L) - \omega t)} \quad (10)$$

$$u(x, z) = \sum_{\mu=1}^{3N} \alpha_\mu \overline{u}_\mu(z) e^{i(k_\mu x - \omega t)} + \sum_{\mu=3N+1}^{6N} \alpha_\mu \overline{u}_\mu(z) e^{i(k_\mu(x-L) - \omega t)} \quad (11)$$

Figure 14:
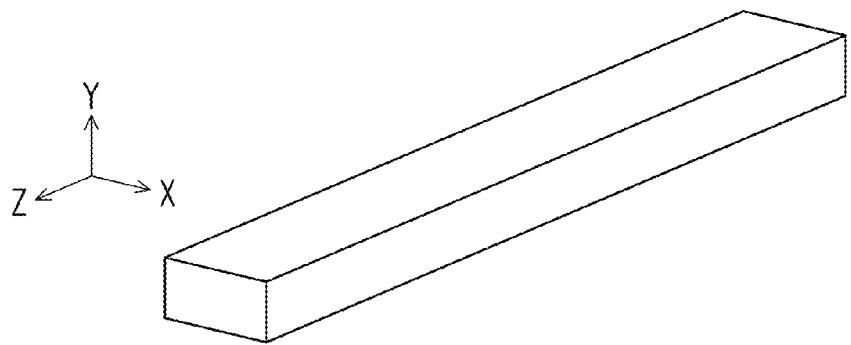
FIG. 14 shows a non-limiting example of a bar structure subjected to analysis for conceptualizing aspects of the present invention.
Figure 15:
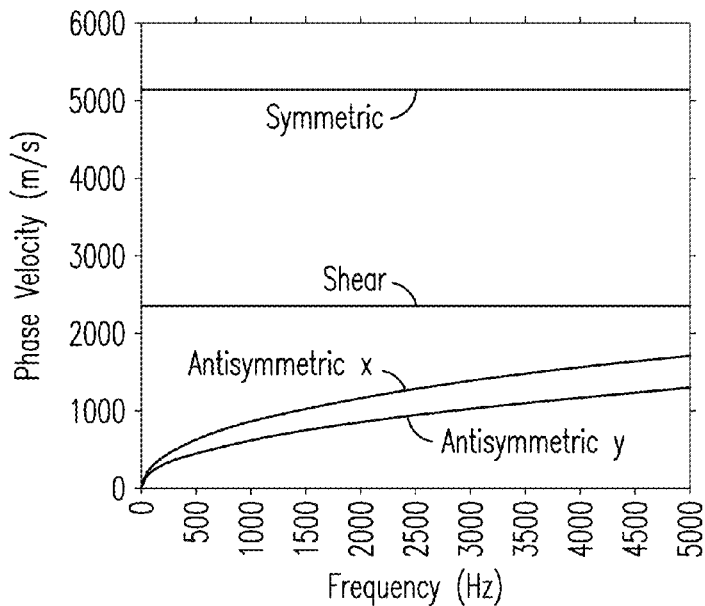
FIG. 15 shows dispersion curves for the bar structure of FIG. 14.
Figure 16:
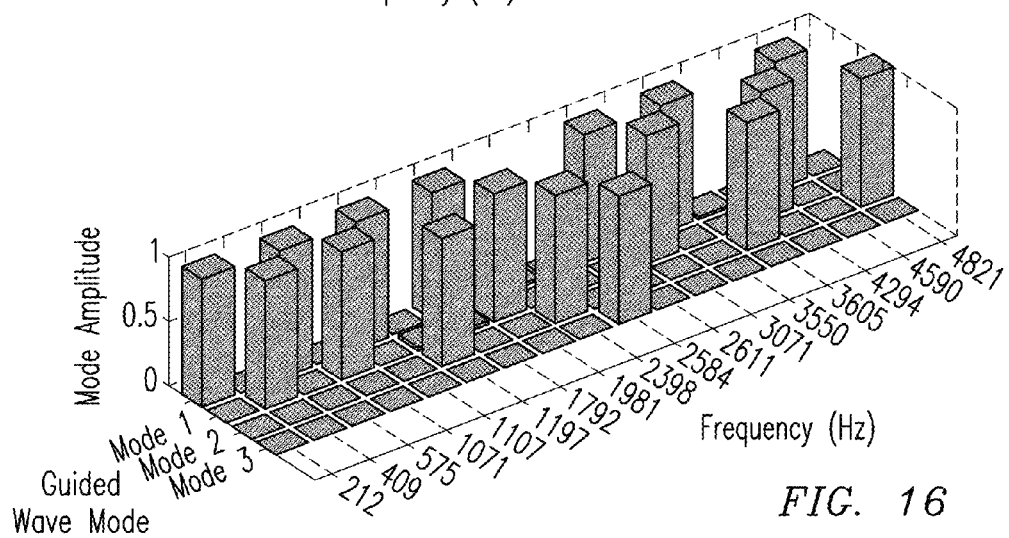
FIG. 16 is a plot of a relative amplitudes of non-limiting examples of guided wave modes associated with the natural resonances of the bar structure of FIG. 14.

Results for the guided wave vibration in the case of a bar structure with rectangular cross-section as shown in FIG. 14 are illustrated in FIG. 15 and table 1 below. Table 1 lists resonant frequencies for the bar structure of FIG. 14 calculated by solving a finite-element eigenvalue problem and by a guided wave vibration analysis. It will be appreciated a relative close numerical approximation between the resonant frequencies of the bar structure and the guided wave vibrations.

program product accessible from a processor-usable or processor-readable medium providing program code for use by or in connection with a processor or any instruction execution system. Non-limiting examples of processor-readable media may include non-transitory tangible processor-readable media, such as a semiconductor or solid-state memory, magnetic tape, a removable computer diskette, a random access memory (RAM), a read-only memory (ROM), a rigid magnetic disk and an optical disk. Present non-limiting examples of optical disks include compact disk-read only memory (CD-ROM), compact disk-read/write (CD-R/W) and DVD.

While various embodiments of the present invention have been shown and described herein, it will be apparent that such embodiments are provided by way of example only. Numerous variations, changes and substitutions may be made without departing from the invention herein. Accordingly, it is intended that the invention be limited only by the spirit and scope of the appended claims.

The invention claimed is:

1. A method to inspect a structure, the method comprising:
    transmitting guided sonic or ultrasonic waves controlled to directionally selectively focus energy to any desired region throughout the structure, wherein the energy is sufficient to cause a thermal response indicative of a structural flaw which may be located at the at least one region of the structure;
    identifying guided wave modes that meet boundary conditions of the structure;
    selectively forming at least one of the identified guided wave modes that meets the boundary conditions of the structure; and
    sensing the thermal response indicative of the flaw.

TABLE 1

| Steady State Vibration | | Resonant Frequencies | | | | Guided Wave Amplitudes | | | | |
| --- | --- | --- | --- | --- | --- | --- | --- | --- | --- | --- |
| Vib. Mode Type | Vib. Mode Order | FEM_lim | FEM_mesh | GW Vib | % error | GW 1 ($A_y$) | GW 2 ($A_x$) | GW 3 (SH) | GW 4 (S) | Match? |
| Flexural | $1_y$ | 211 | 209 | 212 | 0.47% | 1 | 0.01 | 0.01 | 0 | ✓ |
| Flexural | $1_x$ | 408 | 405 | 409 | 0.25% | 0 | 1 | 0 | 0 | ✓ |
| Flexural | $2_y$ | 573 | 569 | 575 | 0.35% | 1 | 0 | 0 | 0 | ✓ |
| Flexural | $2_x$ | 1069 | 1062 | 1071 | 0.19% | 0.01 | 1 | 0 | 0 | ✓ |
| Flexural | $3_y$ | 1103 | 1097 | 1107 | 0.36% | 1 | 0 | 0.01 | 0 | ✓ |
| Torsional | 1 | 1189 | 1167 | 1197 | 0.67% | 0 | 0.02 | 1 | 0 | ✓ |
| Flexural | $4_y$ | 1785 | 1774 | 1792 | 0.39% | 1 | 0.03 | 0.01 | 0 | ✓ |
| Flexural | $3_x$ | 1976 | 1965 | 1981 | 0.25% | 0 | 1 | 0 | 0 | ✓ |
| Torsional | 2 | 2382 | 2337 | 2398 | 0.67% | 0.01 | 0.01 | 1 | 0.01 | ✓ |
| Compressional | 1 | 2583 | 2583 | 2584 | 0.04% | 0 | 0 | 0 | 1 | ✓ |
| Flexural | $5_y$ | 2602 | 2586 | 2611 | 0.35% | 1 | 0 | 0 | 0 | ✓ |
| Flexural | $4_x$ | 3063 | 3047 | 3071 | 0.26% | 0 | 1 | 0 | 0 | ✓ |
| Flexural | $6_y$ | 3536 | 3513 | 3550 | 0.40% | 1 | 0 | 0 | 0 | ✓ |
| Torsional | 3 | 3581 | 3516 | 3605 | 0.67% | 0.01 | 0.01 | 1 | 0 | ✓ |
| Flexural | $5_x$ | 4281 | 4260 | 4294 | 0.30% | 0.01 | 1 | 0.01 | 0.01 | ✓ |
| Flexural | $7_y$ | 4573 | 4548 | 4590 | 0.37% | 1 | 0 | 0 | 0 | ✓ |
| Torsional | 4 | 4788 | 4694 | 4821 | 0.69% | 0 | 0.01 | 1 | 0 | ✓ |

It will be appreciated that aspects of an example inventive guided wave thermography system—which may be used to non-destructively inspect structural flaws in various structures—and methods disclosed herein may be implemented by any appropriate processor system using any appropriate programming language or programming technique. The system can take the form of any appropriate circuitry, such as may involve a hardware embodiment, a software embodiment or an embodiment comprising both hardware and software elements. In one non-limiting embodiment, the system may be implemented by way of software and hardware (e.g., processor, sensors, etc), which may include but is not limited to firmware, resident software, microcode, etc. Furthermore, parts of the processor system can take the form of a computer 2. The method of claim 1, further comprising controlling at least one parameter of at least one signal applied to at least one transmitting transducer having at least one transmitting element for generating the waves, wherein the at least one parameter is selected from the group consisting of a phase delay, a frequency and a combination of phase delays and frequencies.

3. The method of claim 2, further comprising generating a first guided wave excitation which is effective to generate energy having an excitation characteristic effective to enhance detection of a suspected structural flaw geometry at the at least one region of the structure.

4. The method of claim 3, further comprising generating a further guided wave excitation which is effective to apply to the at least one region of the structure further sonic or ultrasonic energy having a different excitation characteristic.

5. The method of claim 4, wherein the further energy is interspersedly applied to the same region of the structure at which the energy generated with the first guided wave excitation is applied.

6. The method of claim 4, wherein the further energy is simultaneously applied to the same region of the structure with the energy generated with the first guided wave excitation.

7. The method of claim 6, wherein the excitation characteristic of the first guided wave excitation is configured to compress opposed edges of a structural flaw at the at least one region of the structure, and the excitation characteristic of the further guided wave excitation is configured to shear said edges.

8. The method of claim 2, wherein the at least one signal for generating the guided sonic or ultrasonic waves comprises a stream of pulses.

9. The method of claim 8, wherein the sensing of the thermal response is synchronized relative to a frequency of the stream of pulses.

10. The method of claim 1, wherein the structure comprises a multi-part structure having different vibrational tolerances, and wherein the method further comprises controlling the guided sonic or ultrasonic waves so that sonic or ultrasonic energy delivered to a region other than the at least one region of the structure is below the vibrational tolerance of the other region of the structure.

11. The method of claim 1, wherein the sensing of the thermal response is synchronized relative to an expected energization time of the at least one region of the structure in response to the guided sonic or ultrasonic waves.

12. A method to inspect a structure, the method comprising:
  selectively steering guided sonic or ultrasonic waves to directionally selectively deliver energy to any desired region throughout the structure, wherein the energy is effective to cause a thermal response upon impingement with a structural flaw which may be located in the structure;
  identifying guided wave modes that meet boundary conditions of the structure;
  selectively forming at least one of the identified guided wave modes that meets the boundary conditions of the structure; and
  sensing the thermal response indicative of the flaw.

13. The method of claim 12, further comprising applying at least one signal to at least one transmitting transducer having at least one transmitting element for generating the waves, wherein the at least one signal comprises a stream of pulses.

14. The method of claim 13, wherein the sensing of the thermal response is synchronized relative to a frequency of the stream of pulses.

15. The method of claim 13, further comprising controlling at least one parameter of the at least one signal applied to the at least one transmitting transducer, wherein the at least one parameter is selected from the group consisting of a phase delay, a frequency and a combination of phase delays and frequencies.

16. The method of claim 15, further comprising generating a first guided wave excitation which is effective to generate energy comprising an excitation characteristic effective to enhance detection of a structural flaw having a first geometry.

17. The method of claim 16, further comprising generating a further guided wave excitation which is effective to generate further sonic or ultrasonic energy having a further excitation characteristic effective to enhance detection of a structural flaw having a further geometry, which is different than the first geometry, wherein the further energy is simultaneously or interspersedly applied to the at least one region of the structure at which the energy generated with the first guided wave excitation is applied.

18. The method of claim 12, further comprising controlling the sensing of the thermal response based on an expected energization profile throughout the structure in response to the guided sonic or ultrasonic waves.

19. The method of claim 18, wherein the controlling of the sensing of the thermal response comprises controlling at least one thermal imaging sensor to dynamically track throughout the structure the expected energization profile.

20. The method of claim 12, wherein the structure comprises a multi-part structure having different vibrational tolerances, and wherein the method further comprises controlling the waves so that energy delivered to multiple regions of the structure is below respective vibrational tolerances of the multiple regions of the structure.

21. A system to inspect a structure, the system comprising:
  at least one transmitting transducer having at least one transmitting element to transmit guided sonic or ultrasonic waves selectively steerable in any desired steering direction to deliver energy to any desired region throughout the structure, wherein the energy is effective to cause a thermal response upon impingement with a structural flaw which may be located in the structure, wherein said at least one transmitting transducer is selectively controlled to form at least one of a plurality of guided wave modes that meets boundary conditions of the structure;
  at least one thermal imaging sensor arranged to sense the thermal response indicative of the flaw; and
  a thermal imaging controller to control sensing of the thermal response by the thermal imaging sensor based on an expected energization profile throughout the structure in response to the guided sonic or ultrasonic waves.

22. The system of claim 21, wherein the at least one thermal imaging sensor comprises a scanning module responsive to the thermal imaging controller so that sensing optics in the at least one thermal imaging sensor dynamically tracks throughout the structure the expected energization profile of the guided sonic or ultrasonic waves.

23. The system of claim 21, further comprising a controller to control at least one parameter of at least one signal applied to the at least one transmitting transducer to generate the guided sonic or ultrasonic waves, wherein the at least one signal comprises a stream of pulses.

24. The system of claim 23, wherein the at least one parameter is selected from the group consisting of a phase delay, a frequency and a combination of phase delays and frequencies.

* * * * *